United States Patent [19]

El Hage

[11] Patent Number: 4,978,213

[45] Date of Patent: Dec. 18, 1990

[54] APPARATUS FOR DETERMINING THE CONTOUR OF THE CORNEA OF A HUMAN EYE

[76] Inventor: Sami G. El Hage, 5417 Del Monte, Houston, Tex. 77056

[21] Appl. No.: 322,680

[22] Filed: Mar. 13, 1989

Related U.S. Application Data

[63] Continuation of Ser. No. 89,535, Aug. 26, 1987, abandoned.

[51] Int. Cl.$^5$ ................................................ A61B 3/10
[52] U.S. Cl. .................................................... 351/212
[58] Field of Search ........................ 351/206, 212, 245

[56] References Cited

U.S. PATENT DOCUMENTS 3,797,921  3/1974  Kilmer et al. ...................... 351/212
4,569,576  2/1986  Karpor et al. ..................... 351/212

Primary Examiner—Paul M. Dzierzynski
Attorney, Agent, or Firm—Vaden, Eickenroht, Thompson & Boulware

[57] ABSTRACT

There is disclosed apparatus which comprises a corneal topographer including a video camera or charge-coupled-device camera system for sensing images of rings of light reflected from the cornea, and means for processing the image rings to produce data useful in determining the contour of the cornea of a human eye.

8 Claims, 3 Drawing Sheets

APPARATUS FOR DETERMINING THE CONTOUR OF THE CORNEA OF A HUMAN EYE this is a continuation, division, of application Ser. No. 07/089,535 now abandoned, filed Aug. 26, 1987

This invention relates generally to apparatus for use in determining the contour of the cornea of a human eye and thus fascilitating the design and fitting of contact lens as well as the performance of surgical procedures. More particularly, it relates to improvements in apparatus of this type which includes a corneal topographer.

In conventional photokeratoscopes used for measuring the contour of the cornea, concentric rings of light from a source of light within a housing are directed onto a cornea and reflected by the cornea onto the film of a camera as an image of the rings. The deviation of the rings from their known concentricity can be measured on the film and this data processed mathematically to determine the contour of the cornea, which of course is not a perfect sphere and which differs from one individual to another.

U.S. Pat. No. 3,248,162 shows a relatively early photokeratosope comprising a cylindrical cage whose inner surface is provided with thin rings of reflective material, and a light source located within the cage so as to reflect light onto the cornea of an eye having its optical axis located coaxially of the cage adjacent its outer end. The light is then reflected from the cornea through the lens of a camera also located coaxially of the cage and thus onto the film of the camera at the inner end of the cage. The reflective rings on the inner surface of the cage are spaced axially distances which decrease in a direction toward its outer end and the eye so that the image rings are substantially equally spaced in a radial direction so as to maximize their number and thus optimize the accuracy of the measurements to be made.

U.S. Pat. No. 3,598,478 shows a subsequent photokeratoscope which is of more compact construction in that rings of light are directed onto the cornea of the eye through transparent slits formed in the opaque surfaces of opposed, generally frusto conically shaped shells from a light source located outside of the innermost shell. Thus, the "target" formed by the shells is shorter than the cylindrical cage of the aforementioned U.S. Pat. No. 3,248,162 and has a small outer end adjacent the cornea to be measured which reduces the loss of light. However, the construction of the target and, in particular, the shape of the inner surfaces of the shells in which the slits are formed, is quite complex, apparently because of the desire for thin slits and thus thin image rings, as well as the desire to cause the light rings to be transmitted to surfaces on the cornea at a right angle with respect thereto.

In use of apparatus of this type, the chin of the individual whose cornea is to be examined is located in a position in which its optical axis is at least approximately aligned with the axis of the target of rings and the lens of the camera. The deviation of this optical axis from alignment can be determined, and, although the calculations for determining its contour do not require absolute alignment, it is desirable that it be as closely aligned as possible in the interest of a more accurate determination. In order to avoid relocating the chin of the individual whose cornea is to be examined, and to bring the axis of the image rings into substantial alignment with the optical axis of the eye, the target and optical system of the camera are preferably adjustable with respect to the chin rest. French Patent No. 7122413 shows a photokeratoscope in which such adjustment may be made by a "joy stick" conventionally located for use by the operator of the photokeratoscope.

Determination of the contour of the cornea with photokeratoscopes of this type has been basically a two step procedure. First, the photograph of the image rings is developed and enlarged, and the images are then processed by appropriate measurements of the spacing between the rings along radial directions, from which a determination of the contour of the cornea may be made by known mathematical calculations. In the interest of permitting these measurements to be made as accurately as possible, the slits and the reflected light rings, and thus their images, should be maintained as thin as possible.

Presently, contact lenses are fitted on the basis of the measurement of the central corneal curvature (about 3 mm in diameter) leaving the peripheral area unknown. It is thus necessary to select lenses from different trial sets until the "quasi" appropriate one is found. This is a tedious procedure that requires a long time (30 to 40 minutes) and a wide variety of trial cases. Contact lenses, thus fitted, require various modifications after they are ordered from the laboratory to be adapted to each cornea. Because of imprecision of the geometry, and poor quality of the finished lens, some patients cannot tolerate them.

If a contact lens is to be designed on the spot and without a return trip of the patient, there is a need for permitting the images to be processed and a determination to be made on a much quicker basis.

Apparatus in which the data may be processed more efficiently is also urgently needed in the performance of certain surgical procedures such as radial keratotomy wherein micro incisions are placed on the cornea in an attempt to surgically modify the curvature of the cornea, and thereby reduce or eliminate myopia and/or astigmatism. Thus, the accuracy of this procedure depends to some degree on the ability to measure the original curvature of the cornea. Although radial keratotomy has become more and more refinable, corneal topography has been largely ignored. Standard keratometry has been utilized to predict the amount of correction available and to some degree the amount of surgery required. Standard keratometry is simply an average of a reflected image assuming the surface measured between points to act geometrically as a sphere. Since the cornea is aspheric, the measurements are inaccurate and therefore the corneal topography is unknown. Better instrumentation to measure true corneal topography would be invaluable in continuing to increase the accuracy of radial keratotomy.

Such apparatus would also be especially useful in myopic and hyperopic keratomileusis in which corneal curvature is altered to improve refractive error by removal of a corneal "disc" of predicted thickness with a microkertome. Tissue dimensions are measured and entered into a computer to generate the settings for a cryolathe, which is used to freeze and remove precise amounts of tissue from the corneal disc so that when the disc is sewn back onto the eye, there is a resultant correction of corneal topography. The alteration of corneal curvature to improve refractive error may also be accomplished with the use of "donor" corneal tissue which is modified with a cryolathe to obtain dimensions which, when sewn onto the host eye, result in a curvature which reduces or eliminates refractive error. Such apparatus would also be especially useful in corneal transplantation which is performed for scarred or diseased corneas by replacing optically inferior cornea tissue with clear tissue. Sutures are placed strategically so that the tissue heals in the most spherical fashion without astigmatism, and suture removal is titrated to promote sphericity, and the surgeon makes judgment of suture removal based on corneal topography.

Such apparatus would be further useful in the intraocular removal of a cloudy lens and subsequent placement of an intraocular lens, wherein, after entering the eye, the wound and sutures are manipulated so as to reduce astigmatism. Corneal topography provides the surgeon with information on how to close the wound and how tight to make the sutures and to measure the power of the intra-ocular lens.

It is therefore the primary object of this invention to provide apparatus of this type which enables the determination of the entire surface of the cornea to be made on an essentially "on line, near real time" basis. Another object is to provide a corneal topographer which is particularly well suited for use as a part of such apparatus, and which, because of the means by which the image rings are processed, has a target that is of less complex and expensive construction that the targets of prior photokeratoscopes. A still further object is to provide such a corneal topographer having means by which the axis of the target and optical axis of the camera may be easily and accurately adjusted to a position substantially aligned with the optical axis of the eye.

In accordance with one novel aspect of the present invention, the apparatus includes a corneal topographer having a video camera or charge-coupled-device camera system on which images of the reflected rings may be sensed and displayed on monitor n, and means preferably comprising relatively inexpensive, off-the-shelf equipment by which the image rings may be processed in order to enable determination of the cornea's contour without manual interventions and in accordance with established mathematical calculations on an essentially on line, near real time basis. Thus, although the screen of the camera is inherently less capable of the precise spatial definition of film, the images rings are processed in a manner which makes it possible to recover the high resolution required in the mathematical calculations.

Thus, the corneal topographer of the apparatus of the present invention is of such construction that the image rings are several times thicker than minimum unit of measurement or "pixel" size of the image processor so that it is possible to digitally produce data sets which represent intensity profiles of the image rings from which the center of the rings may be determined with higher precision than was possible with the manual measurements made with prior apparatus. Upon microscopic examination, the profile of an image ring will vary in intensity from low levels at its edges to a peak in the center, and the digital image processor measures the intensity at several points across the profile of the ring—i.e., the signal strength of each pixel—and fits a mathematical curve to these points to produce a profile. With the intensity profile, once the curve is fitted, the image is no longer required since the data representing the profile has been stored in the processor's memory.

In accordance with another novel aspect of the present invention, the corneal topographer includes a target comprising a body of transparent material having a frusto conically shaped opening therethrough and disposed within a housing with its larger end adjacent the open end of the housing opposite which the cornea of the eye to be examined is positioned. The inner surface of the opening has an opaque covering which is interrupted along its length to form spaced apart, coaxial transparent slits, and a light source is disposed within a space of the housing on the inner end of the body which is enclosed to confine the transmission of light and thus as rings onto the cornea from which the rings are reflected through the lens of the camera.

Thus, as compared with the targets of prior photokeratoscopes, such as that of U.S. Pat. No. 3,598,478, no effort is made to make the slits extremely narrow, and in fact they are purposely rather thick. That is, since resolution is recovered during image processing, no effort need be made to accurately relate the angle of the transmitted ring of light to the surface of the cornea, and the inner surface of the target in which the slits are formed is frusto conical so that the target body itself is easy to form. Preferably, the body has an outer cylindrical surface which is coaxial with the opening and an inner end surface which is perpendicular thereto and opposite the light source, which may be a series of lights spaced equally about the axis. This shape is believed to give more uniform distribution of the light resulting from a more uniform absorption of the light source than would be possible, for example, with a funnel shaped body. Although the preferred shape requires : ore material, it may be cast rather than machined.

In accordance with a still further novel aspect of the invention, the housing of the corneal topographer is mounted on a base of such construction as to permit the housing and thus the target to be moved in each lateral direction as well as vertically. More particularly, the base comprises support bodies which are disposed above and relatively movable with respect to one another to provide a very compact construction.

In the drawings, wherein like reference characters are used throughout to designate like parts:

Figure 1:
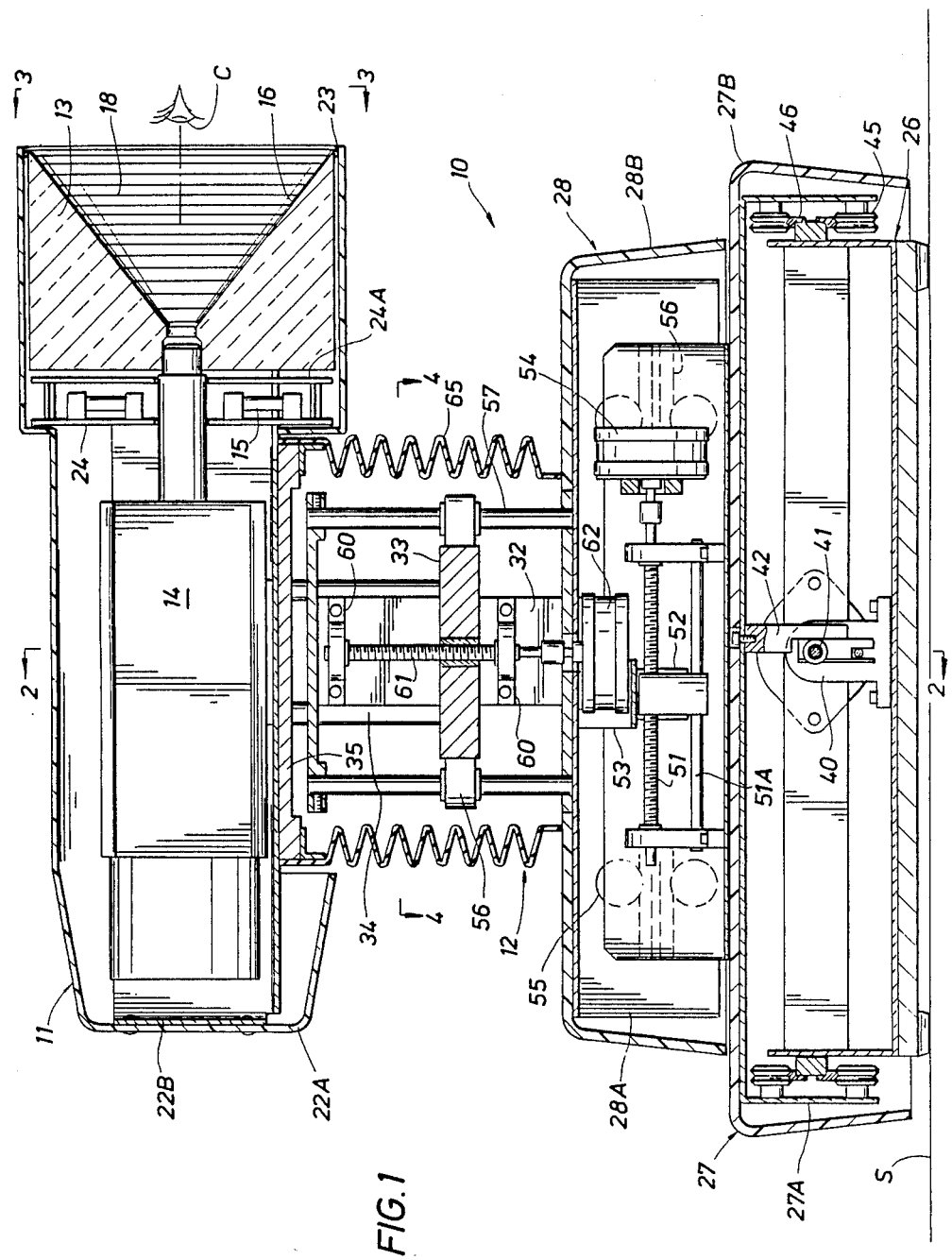
FIG. 1 is a vertical sectional view through a corneal topographer constructed in accordance with the present invention.
Figure 2:
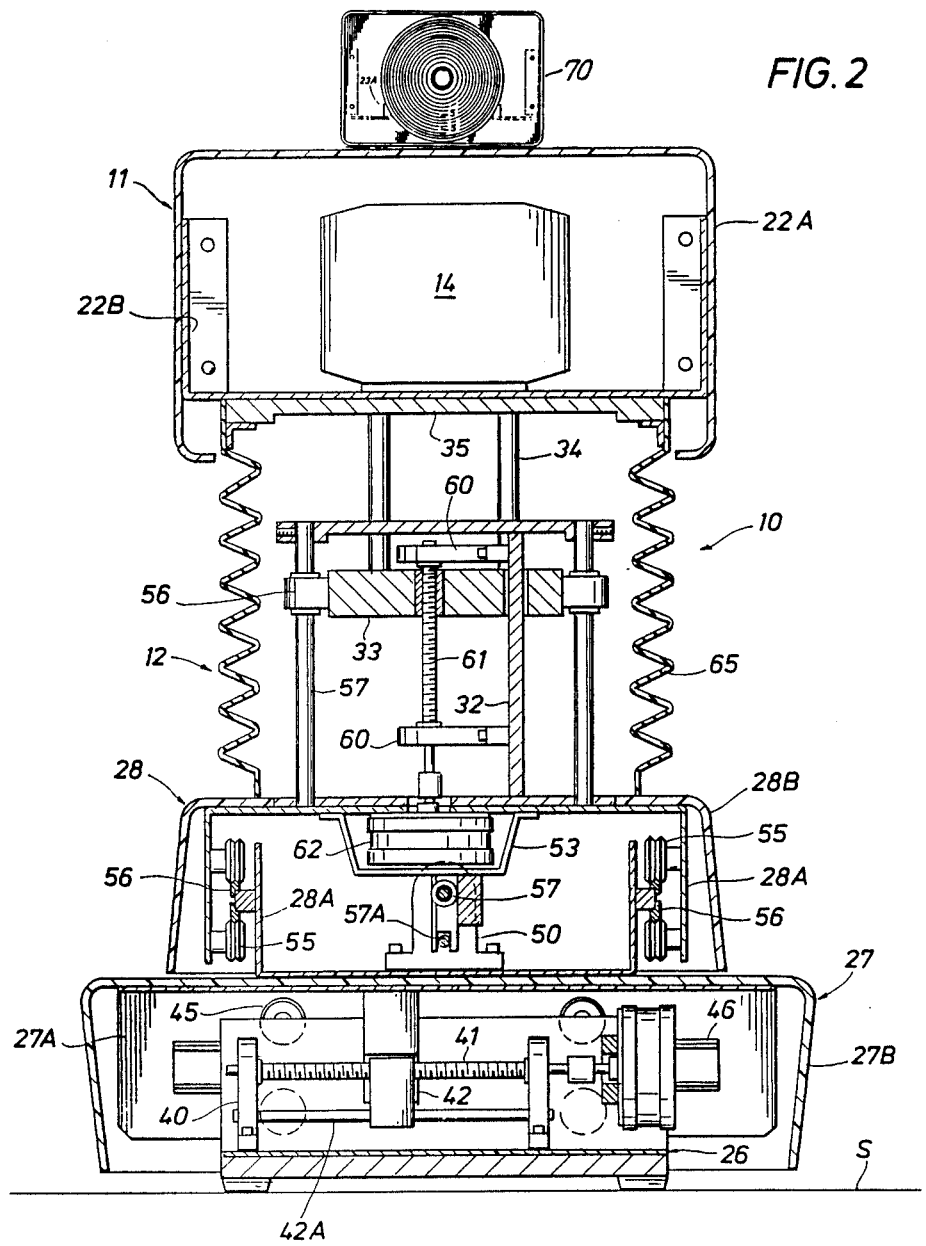
FIG. 2 is a vertical sectional view of the corneal topographer of FIG. 1, as seen along broken lines 2—2 thereof.
Figure 5:
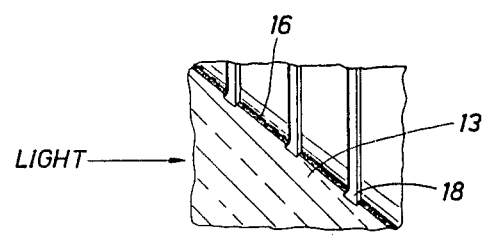
FIG. 5 is an enlarged detailed cross-sectional view of the inner surface of the opening of the target mounted within the housing of the corneal topographer, and showing the slits in the opaque covering on the inner surface of the target opening.

With reference now to the details of the above described drawings, the corneal topographer, which is indicated in its entirety by reference character 10, is best shown in FIGS. 1 and 2 to comprise a housing 11 having an open, right-hand end and supported on a flat surface S by means of a base 12. A target 13 is mounted within the housing adjacent its inner end, a camera 14 is mounted in the housing behind the target, and a light source 15 is mounted in the housing intermediate the rear-end of the target and the front end of the camera.

As previously described, the target 13 comprises a body of transparent material, such as hard plastic, having a frusto conically shaped opening 16 therethrough whose large end faces the right-hand open end of the housing. The inner surface of the opening 16 is covered with opaque material 17 which is interrupted along its length to form coaxial slits 18 through which rings of light from the source 15 may be transmitted onto the cornea C of a human eye located with its optical axis generally aligned with the axis of the opening and thus in substantial axial alignment with the concentric slits 18 and thus the rings of light transmitted through the slits. More particularly, the transmitted rings of light are reflected by the cornea back through a hole 20 in the small end of the opening in which the lens 21 of the camera fits and thus focused as an image onto a planar surface or screen of the video camera 14 or charge-coupled-device camera system.

Figure 3:
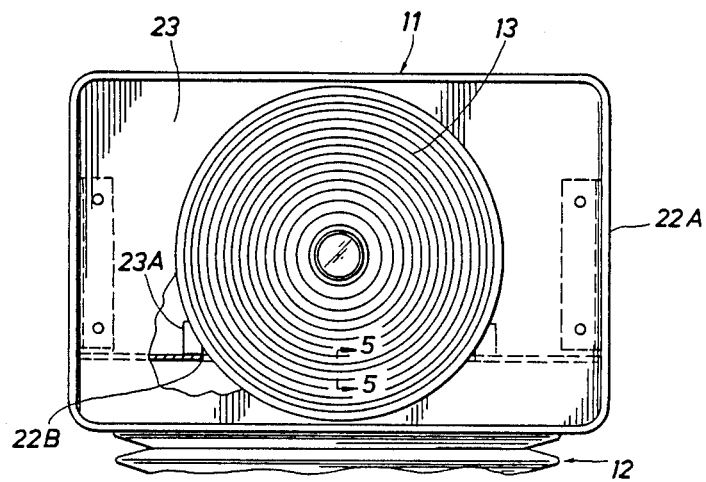
FIG. 3 is a front elevational view of the front end of the housing of the corneal topographer, as seen from broken lines 3—3 of FIG. 1.

The housing includes an outer shell 22A which is open at its front end, and the camera is mounted within the housing by means of a U-shaped bracket 22B fastened to the outer shell and extending lengthwise thereof into the open end of the outer shell on opposite sides of the body 13. The housing also includes a face plate 23 having an opening therethrough to closely receive the outer end of the target, and adapted to be attached to the front end of the bracket 22 by fasteners 23A (FIG. 3).

The light source 15 comprises a series of equally spaced lamps arranged about the lense 21 and mounted on a bracket 24 fixed to the front end of the camera and having a light diffuser 24A on its front side. As can be understood from the foregoing, the housing thus provides an enclosure which confines substantially all of the light from the source 15 to pass through the slits in the body of the target 13, and thus as rings to be transmitted to and reflected from the cornea of the eye. As shown, the slits are spaced apart different distances which decrease in a direction toward the eye so that the image rings which are sensed on the planar surface of the camera are substantially equally radially spaced apart.

With reference to the details of the above described components of the base, a pair of journals 40 are supported on the bottom wall of the pedestal 26 in spaced apart relation, and a lead screw 41 is supported at its opposite ends from the journals. The lead screw is threadedly received through a follower block 42 connected to and depending from the top wall of the member 27A, and held against rotation by a guide rod 42A, and the lead screw is adapted to be rotated in opposite directions by means of a reversible motor 43 supported on a sidewall of the pedestal in opposite directions. Thus, upon rotation of the motor 43, the follower block 42 and thus the first body may be moved in opposite directions laterally of the support surface S. More particularly, rollers 45 are carried by the sidewalls of the member 27A for movement along upper and lower tracks 46 on the outer sides of the side walls of the pedestal, thus supporting the body 27 for guided lateral movement with respect to the pedestal.

The base 12 of the corneal topographer includes a pedestal 25 comprising a generally "U" shaped member 26 having a bottom wall adapted to be supported on a horizontal surface S, and a first or lower body 27 which is supported on the pedestal for guided movement laterally with respect thereto, and thus with respect to the surface S, in a first lateral direction. The first body includes an inverted "U" shaped member 27A having a top wall disposed over the pedestal and side walls depending therefrom on the outer sides of the side walls of the pedestal, and an inverted "U" shaped cover 27B having a top wall connected to the top wall of member 27A and having side walls depending therefrom along the side walls as well as over the open ends of the pedestal and member 27A.

The base 12 also includes a second or upper body 28 which includes an inverted "U" shaped member 28A having a top wall which is disposed over and supported by a "U" shaped member 27C connected to the top wall of the cover 27B for guided movement laterally with respect thereto in a lateral direction perpendicular to the direction in which the body may be moved. Similarly to the member 27A, the member 28A also has side walls which depend therefrom on the outer sides of the side walls of member 27C. Body 28 further includes a cover 28B similar to cover 27B and having a top wall connected to the top wall of member 28A, and side walls which depend from the top wall along the outer sides of the side walls as well as the open sides of the members 27C and 28A.

The second body 29 is supported from and moved in another lateral direction with respect to the first body 27 in a manner similar to that described above. Thus, a pair of journals 50 which are mounted in spaced apart relation on the "U" shaped member 27C connected to the top wall of the cover 27B, and a lead screw 51 is supported at its opposite ends within the journals. A follower block 52 is threadedly connected to the lead screw and supported by means of a bracket 53 connected to the lower side of the top wall of member 28A, and a reversible motor 54 is mounted on the member 27C to rotate the lead screw 51 and thus move the block 52 which is held against rotation by a guide rod 52A, and member 28 laterally with respect to the body 27, as seen in the plane of FIG. 1. In addition, rollers 55 are mounted on the inner sides of the side walls of the member 28A for guided movement along upper and lower tracks 56 mounted on the outer sides of the side way of member 27C for supporting the body 28 for guided movement laterally with respect to the body 27.

Figure 4:
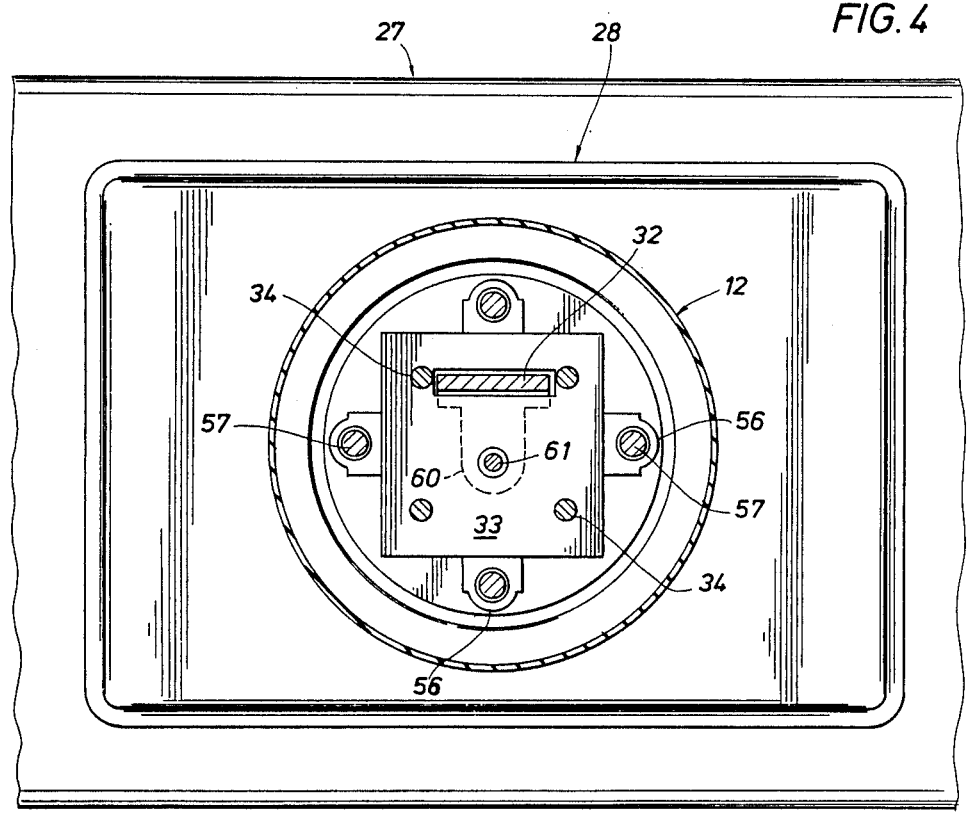
FIG. 4 is a horizontal sectional view of the corneal topographer, as seen along broken lines 4—4 of FIG. 1 thereof.

The bracket 32 is shown in FIG. 4 to pass upwardly through a hole in the platform 33, and, sleeves 56 are mounted on opposite sides of the platform 33 for guided movement vertically along post 57 which are mounted at their lower ends on the top wall of the cover 28B and which connect at their upper ends to a top wall 57A which is disposed beneath the upper wall 35 on which the housing is supported. Journals 60 are mounted on the side of the wall 32 in spaced apart relation, and a lead screw 61 is supported at opposite ends by the journals. The lead screw extends threadedly through a hole in the bracket 33 and is adapted to be rotated by means of a reversible motor 62 which is received within the bracket 53 beneath the top wall of the member 28A, with its shaft extending through the member. Thus, rotation of the motor will cause the platform 33 to move vertically along the lead screw 61 and thus raise or lower the housing with respect to the body 28. A bellows 65 surrounds the parts above described and is connected at its opposite ends to the wall 35 and the top wall 28B of the body 28, thereby protecting the parts against dust or other environmental debris.

In accordance with the preferred embodiment of the invention, each of the motors is a step motor to permit incremental adjustments of the housing in both lateral directions as well as vertically. Each motor is individually operated to permit each adjustment to be made independently of the other.

As previously indicated, the geometry upon which the mathematical calculations are based assumes that the optical axis of the cornea is aligned with the axes of the camera and target and thus the rings of light which are transmitted from the target. Although the chin of the person to be examined may be carefully placed in relation to the corneal topographer, absolute alignment is of course impossible even with the assistance of the fine adjustments made possible by the base on which the housing is mounted.

In any event, with the cornea located as near as possible to the desired axis, and the base suitably adjusted, the camera is actuated to take a shot, and the image processor determines how far the optical axis is from the desired axis by superimposing an image of the optical axis upon the image rings. Thus the operator of the apparatus is able to see this image on the monitor screen of the computer, and by suitable programming, compensation may be made for the displacement of the optical axis from the desired axis in order to adjust all image data as if the optical axis were precisely aligned.

As previously described, the overall apparatus permits determination of the contour of the cornea on an on-line, near real time basis. Thus, for this purpose, a conventional, off-the-shelf image processor may be installed within the computer and connected to the output of the video camera or a charge-coupled-device camera system to take standard video signals, digitize them, and convert the image rings into digital data sets. Although the target is of such construction that the image rings are relatively thick, the system is such that definition of the rings is retrieved during their processing. In fact, and as previously mentioned, the image processor is uniquely suited to the thick image rings in that the profiles of the rings are several times the width of a relatively large number of pixels or minimum measuring units of the processor, thereby permitting determination of the contour with fine resolution. Thus, the present invention is a radical departure from the prior art wherein the targets were of complex construction in order to provide the thinnest possible image rings, which in turn was necessary in order to obtain greater resolution on the film cf the rings taken by the camera of the system.

From the foregoing it will be seen that this invention is one well adapted to attain all of the ends and objects hereinabove set forth, together with other advantages which are obvious and which are inherent to the apparatus.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. Apparatus for use in determining the contour of the cornea of a human eye, comprising a housing having an open end, a source of light within the housing, means within the housing for transmitting concentric rings of light from the source to the cornea of a human eye located at the open end of the housing, each ring being several pixels wide, camera means having a lens positioned with its optical axis coaxial to the rings of light reflected by the cornea and means to sense and display images of the rings that are reflected by the cornea, means for measuring the intensity of the light of each pixel across a profile of each reflected ring, means for determining the pixel in each ring that has the highest intensity of reflected light, and means for calculating the contour of the cornea using the pixel having the highest intensity of reflected light of each ring of light reflected by the cornea by fitting a mathematical curve to such pixels.

2. The apparatus of claim 1 further provided with means for converting the intensity of the pixel wide rings of each reflected ring to digital sets from which the location of the pixel ring of each reflected ring having the highest intensity of reflected light can be selected for use in calculating the contour of the cornea.

3. The apparatus of claim 1 further provided with means for measuring any misalignment of the optical axis of the camera lens with the axis of the eye and means to compensate for any misalignment of the axes in the calculation of the contour of the cornea.

4. Apparatus for use in determining the contour of the cornea of a human eye, comprising a corneal topographer including a housing having an open end, a source of light within the housing, means within the housing for transmitting concentric rings of light from the source to the cornea of a human eye located at the open end of the housing, each light ring being several pixels wide, means for converting the light rings reflected from the cornea to video signals, means for converting the video signal for each light ring into a plurality of digital values for the light intensity of each pixel across a profile of the light ring, means for determining the pixel having the highest light intensity in each light ring, and means to calculate the contour of the cornea based on the location of the pixel in each light ring having the highest intensity.

5. The apparatus of claim 4 further provided with means for displaying the reflected rings of light on a video monitor.

6. A method of determining the contour of the cornea of a human eye in real time for guiding a surgeon performing surgery on the eye comprising the steps of transmitting concentric rings of light several pixels wide onto the cornea of a human eye, converting the light rings reflected from the eye to video signals, converting the video signals for each ring into digital values for the intensity of each pixel across a profile of each ring, determining the pixel in each ring having the highest intensity of reflected light, and calculating the contour of the eye using the pixel of each reflected ring having the highest intensity.

7. The method of claim 6 further including the step of displaying the video signals on a monitor.

8. The apparatus of claim 1 or 4 in which the means for transmitting concentric rings of light from the source to the cornea of a human eye located at the open end of the housing includes a body of transparent material having a frusto-conically shaped opening therethrough disposed within the housing with its outer, larger end adjacent the open end of the housing, the inner surface of the opening having an opaque covering that is interrupted along its length to form spaced apart, coaxial, transparent slits through which light from the light source is transmitted as concentric rings of light.

* * * * *

REEXAMINATION CERTIFICATE (3153rd)
United States Patent [19]
El Hage

[11] B1 4,978,213
[45] Certificate Issued  Mar. 11, 1997

[54] APPARATUS FOR DETERMINING THE CONTOUR OF THE CORNEA OF A HUMAN EYE

[75] Inventor: Sami G. El Hage, Houston, Tex.

[73] Assignee: Alcon Laboratories, Inc., Fort Worth, Tex.

Reexamination Request:
No. 90/004,136, Feb. 13, 1996

Reexamination Certificate for:
Patent No.: 4,978,213
Issued: Dec. 18, 1990
Appl. No.: 322,680
Filed: Mar. 13, 1989

Related U.S. Application Data

[63] Continuation of Ser. No. 89,535, Aug. 26, 1987, abandoned.

[51] Int. Cl.[6] ........................................ A61B 3/10
[52] U.S. Cl. ................................................ 351/212
[58] Field of Search ................................. 351/205, 206, 351/212, 245

[56] References Cited

U.S. PATENT DOCUMENTS

| | | |
|---|---|---|
| 4,685,140 | 8/1987 | Mount, II ........................... 351/212 X |
| 4,692,003 | 9/1987 | Adachi et al. ......................... 351/212 |
| 4,772,115 | 9/1988 | Gersten et al. ........................ 351/212 |

FOREIGN PATENT DOCUMENTS

| | | |
|---|---|---|
| 137766 | of 1961 | U.S.S.R. . |
| 1292727A1 | 2/1987 | U.S.S.R. . |

*Primary Examiner*—Huy Mai

[57] ABSTRACT

There is disclosed apparatus which comprises a corneal topographer including a video camera or charge-coupled-device camera system for sensing images of rings of light reflected from the cornea, and means for processing the image rings to produce data useful in determining the contour of the cornea of a human eye.

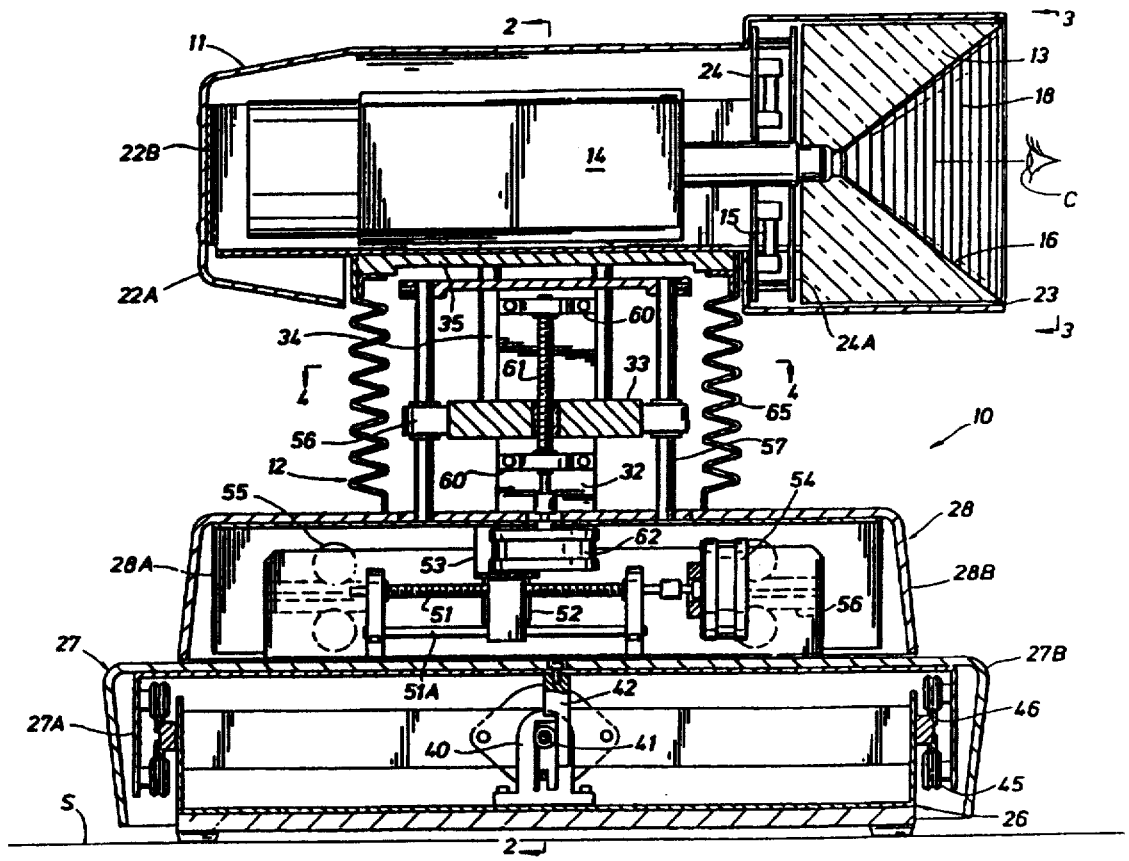

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 4 and 6 are determined to be patentable as amended.

Claims 2, 3, 5, 7 and 8 dependent on an amended claim, are determined to be patentable.

New claims 9–16 are added and determined to be patentable.

1. Apparatus for use in determining the contour of the cornea of a human eye, comprising a housing having an open end, a source of light within the housing, means within the housing for transmitting concentric rings of light from the source of the cornea of a human eye located at the open end of the housing, each ring being several pixels wide, camera means having a lens positioned with its optical axis coaxial to the rings of light reflected by the cornea and means to sense and display images of the rings that are reflected by the cornea, means for measuring the intensity of the light of each pixel across *each of a plurality of profiles of each reflected ring, which plurality of profiles are defined from the inner edge to the outer edge of each reflected ring and are substantially contiguously positioned around the entire 360° C. arc of each reflected ring,* means for determining [the] *a ring-shaped subset of* pixels in each *reflected* ring [that has] *comprising the single pixel from each of the plurality of profiles within that ring having* the highest intensity of reflected light, and means for calculating the contour of the cornea [using the pixel having the highest intensity of reflected light of each ring of light reflected by the cornea] by fitting a mathematical curve to [such] *each ring-shaped subset of pixels*.

4. Apparatus for use in determining the contour of the cornea of a human eye, comprising a corneal topographer including a housing having an open end, a source of light within the housing, means within the housing for transmitting concentric rings of light from the source to the cornea of a human eye located at the open end of the housing, each light ring being several pixels wide, means for converting the light rings reflected from the cornea to video signals, means for converting the video signal for each light ring into a [plurality of] digital value[s] for the light intensity of each pixel across *each of a plurality of* profiles of [the] *each* reflected light ring, *which plurality of profiles are defined from the inner edge to the outer edge of each reflected ring and are substantially contiguously positioned around the entire 360° arc of each reflected ring,* means for determining [the] *a ring-shaped subset of pixels* [having] *comprising the single pixel from each of the plurality of profiles within that ring having* the highest light intensity [in each light ring], and means to calculate the contour of the cornea based on the location of [the pixel in each light ring having the highest intensity] *all ring-shaped subsets of pixels*.

6. A method of determining the contour of the cornea of a human eye in real time for guiding a surgeon performing surgery on the eye comprising the steps of transmitting concentric rings of light several pixels wide onto the cornea of a human eye, converting the light rings reflected from the eye to video signals, converting the video signals for each ring into *a* digital value[s] for the intensity of each pixel across *each of a plurality of* profiles of each reflected ring, *which plurality of profiles are defined from the inner edge to the outer edge of each reflected ring and are substantially contiguously positioned around the entire 360° arc of each reflected ring,* determining [the pixel in] *for* each *reflected* ring *a ring-shaped subset of pixels that is a single pixel wide and comprises the pixels from all the profiles of that ring* having the highest intensity of reflected light *in each profile*, and calculating the contour of the eye using [the pixel of each reflected ring having the highest intensity] *all ring-shaped subsets of pixels*.

9. *The apparatus of claim 3 in which the means for transmitting concentric rings of light from the source to the cornea of a human eye comprises a body of transparent material located within the housing and comprising:* a. *an exterior surface exposed to the source of light;*
   b. *a circular frusto-conical cavity defining:*
      i. *a small opening in a first end of the body,*
      ii. *a large opening in a second end of the body opposite the first end and oriented toward the eye,*
      iii. *an interior surface disposed between the small open end and the large open end, and*
      iv. *a longitudinal axis of symmetry;*
   c. *an opaque covering on the interior surface; and*
   d. *a plurality of circular slits in the opaque covering spaced apart in a direction defined by the longitudinal axis.*

10. *The apparatus of claim 9 in which the exterior surface defines a right circular cylinder symmetric about the longitudinal axis and a base adjacent the light source that is substantially perpendicular to the longitudinal axis and located on the first end of the body.*

11. *The apparatus of claim 8 in which the exterior surface defines a right circular cylinder symmetric about a longitudinal axis of the body of transparent material and a base adjacent the light source that is substantially perpendicular to the longitudinal axis and located on the end of the body defining the smaller end of the frusto-conically shaped opening.*

12. *The method of claim 6 in which the concentric rings are transmitted along a first axis and the light rings reflected from the eye are reflected along a second axis and further comprising the steps of automatically measuring any misalignment between the first axis and the second axis and automatically compensating for the misalignment in the step of calculating the contour of the eye.*

13. *The method of claim 12 in which the step of transmitting concentric rings of light onto the cornea of a human eye is accomplished by:* a. providing a body of transparent material having:
  i. an exterior surface,
  ii. a circular frusto-conical cavity defining an interior surface symmetric about the first axis, a small opening in a first end of the body, and a large opening in a second end of the body opposite the first end,
  iii. an opaque covering on the interior surface, and
  iv. a plurality of circular slits in the opaque covering spaced apart in a direction defined by the first axis;
b. positioning a light source outside the exterior surface; and
c. orienting the large opening toward the eye such that light from the light source passes through the slits and onto the cornea.

14. The method of claim 13 in which the exterior surface of the body defines a right circular cylinder symmetric about the first axis and a base adjacent the light source that is substantially perpendicular to the first axis and located on the first end of the body.

15. The method of claim 6 in which the step of transmitting concentric rings of light onto the cornea of a human eye is accomplished by:

a. providing a body of transparent material having:
  i. an exterior surface,
  ii. a circular frusto-conical cavity defining an interior surface of a longitudinal axis, a small opening in a first end of the body, and a large opening in a second end of the body opposite the first end,
  iii. an opaque covering on the interior surface, and
  iv. a plurality of circular slits in the opaque covering spaced apart in a direction defined by the longitudinal axis;
b. positioning a light source outside the exterior surface; and
c. orienting the large opening toward the eye such that light from the light source passes through the slits and onto the cornea.

16. The method of claim 15 in which the exterior surface of the body defines a right circular cylinder symmetric about the longitudinal axis and a base adjacent the light source that is substantially perpendicular to the longitudinal axis and located on the first end of the body.

* * * * *